(12) United States Patent
Witte et al.

(10) Patent No.: US 10,512,598 B2
(45) Date of Patent: Dec. 24, 2019

(54) LIQUID HAIR DYE WITH OPTIMIZED DYING PERFORMANCE AND CARE

(71) Applicant: Henkel AG & Co. KGaA, Duesseldorf (DE)

(72) Inventors: Christiane Witte, Hetlingen (DE); Stephan Schwartz, Wedel (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/767,318

(22) PCT Filed: Sep. 26, 2016

(86) PCT No.: PCT/EP2016/072818
§ 371 (c)(1),
(2) Date: Apr. 10, 2018

(87) PCT Pub. No.: WO2017/063853
PCT Pub. Date: Apr. 20, 2017

(65) Prior Publication Data
US 2019/0060194 A1     Feb. 28, 2019

(30) Foreign Application Priority Data

Oct. 14, 2015   (DE) .................. 10 2015 219 940

(51) Int. Cl.

| A61Q 5/10 | (2006.01) |
|---|---|
| A61K 8/36 | (2006.01) |
| A61K 8/41 | (2006.01) |
| A61K 8/42 | (2006.01) |
| A61K 8/22 | (2006.01) |
| A61K 8/34 | (2006.01) |
| A61K 8/49 | (2006.01) |
| A61K 8/81 | (2006.01) |
| A61K 8/92 | (2006.01) |

(52) U.S. Cl.
CPC ............. *A61K 8/361* (2013.01); *A61K 8/22* (2013.01); *A61K 8/34* (2013.01); *A61K 8/41* (2013.01); *A61K 8/42* (2013.01); *A61K 8/4973* (2013.01); *A61K 8/8152* (2013.01); *A61K 8/92* (2013.01); *A61Q 5/10* (2013.01); *A61K 2800/262* (2013.01); *A61K 2800/30* (2013.01)

(58) Field of Classification Search
CPC .......... A61Q 5/10; A61K 8/411; A61K 8/415; A61K 8/342; A61K 8/41; A61K 8/42; A61K 8/34; A61K 8/361; A61K 2800/4324; A61K 2800/882
See application file for complete search history.

(56) References Cited

U.S. PATENT DOCUMENTS 4,698,065 A * 10/1987 Hoeffkes .................. A61K 8/45
8/406

FOREIGN PATENT DOCUMENTS

| DE | 3500877 A1 | 7/1986 |
|---|---|---|
| DE | 19756454 C1 | 6/1999 |
| DE | 102013226583 A1 | 6/2015 |
| EP | 0351645 A2 | 1/1990 |
| EP | 1897532 A1 | 3/2008 |
| EP | 2226064 A1 | 9/2010 |
| WO | 9201438 A1 | 2/1992 |
| WO | 2006136277 A1 | 12/2006 |
| WO | 2015090805 A1 | 6/2015 |

OTHER PUBLICATIONS

EPO, International Search Report and Written Opinion issued in International Application No. PCT/EP2016/072818, dated Oct. 14, 2016.

* cited by examiner

*Primary Examiner* — Eisa B Elhilo
(74) *Attorney, Agent, or Firm* — Lorenz & Kopf, LLP

(57) ABSTRACT

The present disclosure relates to a liquid agent and/or hair dye for oxidative coloring of keratinous fibers with improved color performance and nourishing effect. In an embodiment, the agent comprises, in a hydrous cosmetic carrier: (a) a fatty acid which is liquid at 20° C. and has about 16-22 carbon atoms in an amount of about 0.1-15 wt. %, (b) an alkanolamine as an alkalizing agent, selected from monoethanolamine, 2-amino-2-methylpropanol and triethanolamine, in an amount such that at least one part of the fatty acid is present as soap, (c) an oil component different from (a) in an amount of about 0.05-5 wt. %, (d) an alkylamidoamine in an amount of about 0.05-6 wt. %, and (e) an oxidation dye precursor. The agent does not contain any branched fatty alcohols having about 7 or more carbon atoms, and does not contain any fatty alcohols having a melting point of about 25° C. or higher.

20 Claims, No Drawings

LIQUID HAIR DYE WITH OPTIMIZED DYING PERFORMANCE AND CARE

CROSS-REFERENCE TO RELATED APPLICATION

This application a U.S. National-Stage entry under 35 U.S.C. § 371 based on International Application No. PCT/EP2016/072818, filed Sep. 26, 2016 which was published under PCT Article 21(2) and which claims priority to German Application No. 10 2015 219 940.1, filed Oct. 14, 2015, which are all hereby incorporated in their entirety by reference.

TECHNICAL FIELD

The present disclosure relates to a liquid agent and/or a liquid hair dye for oxidative coloring of keratinous fibers, particularly human hair, with improved color performance and outstanding nourishing effect. Furthermore, the present disclosure relates to a combination preparation consisting of the liquid agent and an oxidant preparation, as well as a method for changing the color of keratinous fibers using the liquid agent.

BACKGROUND

Various color systems for preparation of a color-changing cosmetic agent, particularly for keratinous fibers, such as hair, depending on the requirement, are known to the person skilled in the art. For permanent, intense colors with corresponding fastness properties, so-called oxidative dyes normally consisting of two components are used. An alkaline preparation of oxidation dye precursor containing so-called developer components and coupler components, which forms the actual dyes under the influence of oxidants, such as hydrogen peroxide, is used as a first component. The oxidant preparation, which is frequently also referred to as a developer, containing at least water and hydrogen peroxide and adjusted to an acidic value for stability purposes, is uses as a second component.

The oxidant preparation adjusted to an acidic value is mixed with the first component adjusted to an alkaline value shortly before, normally in a weight ratio of first part adjusted to alkaline value to oxidant preparation of from about 1:1 to about 1:2. This application mixture is applied on the hair, normally remains there for approximately 30 to 45 minutes and is then rinsed off. During this time, the oxidation dye precursors react to each other under the influence of the hydrogen peroxide to form oligomers, wherein the desired hair color is developed.

The application mixture should have a viscosity such that it does not drip from the hair during the application time and exposure time, but is not too viscous that it can be mixed homogeneously and be applied easily. In many commercially available hair dye combination preparations, therefore, at least one of the two components, usually the oxidant preparation, contains a thickener, which is only slightly acidic, but thickens increasingly when alkaline, such as polyacrylic acid or polyacrylic ester (for example, see the example compositions disclosed m WO 2006/136277 A1, DE 102012233206 A1 or DE 102013226583 A1) Typical application mixture viscosities are in the range of approximately 3500 mPa s to approximately 10000 mPa s at 20° C. All physical specifications are relative to a pressure of 1013 mbar.

EP 1 897 532 A1 discloses oxidative hair coloring agents in the form of emulsions which have at least one branched fatty alcohol, at least one nonionic emulsifier and at least one alkylamidomine.

Furthermore, in the European area, the oxidation dye precursor containing Component 1 is normally cream-like. Unlike cream-like coloring agents, liquid, clear coloring agents containing oxidation dye precursors achieve a less-intensive color result with the same amount of dye.

Furthermore, ammonia/ammonium hydroxide is often used as an alkalizing agent of the dye containing oxidation dye precursor, because an optimal color result can be achieved in the process, which is based on the outstanding swelling of the hair due to ammonia and the effect of ammonia as a penetrating agent. Ammonia, therefore, is frequently used as an alkalizing agent despite its disturbing odor. Ammonia, as an alkalizing agent, is particularly suitable for cream-like compositions, because less ammonia escaped from cream-like compositions than from liquid compositions.

However, a clear, liquid dye is frequently desired by consumers, particularly American consumers. Therefore, the present disclosure addresses the problem of providing a liquid agent and/or a liquid hair dye for oxidative changing of color of keratinous fibers, particularly human hair, with improved color performance, which does not require addition of ammonia as an alkalizing agent or addition of only a reduced amount of ammonia.

A further aspect of hair coloring system is that a beneficial good nourishing effect should be guaranteed. For this reason, a nurturing oil is normally contained in the cream-like component containing oxidation dye precursors. However, it is more difficult to incorporate a nurturing oil into liquid coloring agents without the liquid becoming cloudy. The present disclosure also addressed the problem of providing a liquid, clear coloring agent for keratinous fibers which has a good nurturing effect on the treated keratinous fibers with application after mixture with an oxidant preparation.

Furthermore, the present disclosure addresses the problem that the liquid agent has or develops a suitable mixture viscosity for coloring of keratinous fibers.

These problems were solved with a composition according to Claim 1. Such liquid coloring agents achieve a suitable application mixture viscosity by mixing with a hydrous oxidant preparation, particularly when the oxidant preparation contains a specific cationic surfactant. Furthermore, the liquid coloring agent has an outstanding, intensive coloring characteristic and a simultaneous good nurturing effect after mixture with an oxidant preparation. The specification "liquid" refers to the aggregate state at 1013 mbar and 20° C.

SUMMARY

In an embodiment, a liquid agent for oxidative coloring of keratinous fibers comprises, in a hydrous cosmetic carrier: (a) a fatty acid which is liquid at 20° C. and has about 16-22 carbon atoms in an amount of about 0.1-15 wt. %, (b) an alkanolamine as an alkalizing agent, selected from monoethanolamine, 2-amino-2-methylpropanol and triethanolamine, in an amount such that at least one part of the fatty acid is present as soap, (c) an oil component different from (a) in an amount of about 0.05-5 wt. %, (d) an alkylamidoamine in an amount of about 0.05-6 wt. %, and (e) an oxidation dye precursor. The agent does not contain any branched fatty alcohols having about 7 or more carbon atoms, and does not contain any fatty alcohols having a melting point of about 25° C. or higher.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

1. A liquid agent for oxidative coloring of keratinous fibers, particularly human hair, which contains, in a hydrous cosmetic carrier:
   (a) at least one fatty acid which is liquid at 20° C. having from about 16 to about 22 carbon atoms in a total amount of from about 0.1 to about 15 wt. %,
   (b) at least one alkanolamine as an alkalizing agent, selected from monoethanolamine, 2-amino-2-methylpropanol and triethanolamine, in an amount such that at least one part of the fatty acid is present in the form of a soap,
   (c) at least one oil component different from (a), in a total amount of from about 0.05 to about 5 wt. %,
   (d) at least one alkylamidoamine in a total amount of from about 0.05 to about 6 wt. % and
   (e) at least one oxidation dye precursor,
   wherein the agent does not contain any fatty alcohols that are branched and has about 7 or more carbon atoms, and does not contain any fatty alcohols that have a melting point of about 25° C. or higher, and
   wherein the quantity specifications are relative to the total weight of the liquid agent in each case.
2. Agent according to point 1 wherein the agent is not present as an emulsion.
3. Agent according to point 1 or 2 wherein the agent has a pH value in the range of from about 8 to about 11, measured at 20° C.
4. Agent according to one of the points above, wherein the alkylamidoamine is selected from stearamidopropyl dimethylamine, cocamidopropyl dimethylamines, ricinoleic amidopropyl dimethylamine, isostearamidopropyl dimethylamine, oleamidopropyl dimethylamine, behamidopropyl dimethylamine, oleamidopropyl dimethylamine quaternium-33, behamidopropyl ethyldimonium ethosulfate and combinations thereof, particularly stearamidopropyl dimethylamine.
5. Agent according to one the points above which additionally contains at least one anionic surfactant that is different from soap, and/or at least one nonionic surfactant.
6. Agent according to one of the preceding points, which does not contain any anionic surfactants except for the fatty acid in the form of a soap.
7. Agent according to one of the points above containing, as a nonionic surfactant, at least one alkyl- and/or alkenyl monoethanolamide with from about 8 to about 18 carbon atoms in the alkyl chain, preferably selected from lauric acid monoethanolamide (INCI: Lauramide MEA) and coconut oil fatty acid methanolamide (INCI: Cocamide MEA), preferably in a total amount of from about 0.5 to about 5 wt. %, more preferably from about 1 to about 3 wt. % relative to the total amount of the liquid agent.
8. Agent according to one of the points above containing, as a nonionic surfactant, an adduct of from about 1 to about 5 mol ethylene oxide on a linear fatty alcohol with from about 8 to about 22 carbon atoms, preferably from about 12 to about 14 carbon atoms, preferably in an amount of from about 5 to about 12 wt. %, more preferably from about 7 to about 10 wt. % relative to the total amount of the liquid agent.
9. Agent according to one of the points above which contains about 0.8 wt. % or less, preferably about 0.4 wt. % or less, more preferably no ammonia, relative to the percentage by weight relative to the liquid agent.
10. Agent according to one of the points above which contains about 0.3 wt. % or less, preferably no fatty substances that are solid at 20° C., relative to the percentage by weight relative to the liquid agent.
11. Agent according to one of the points above which contains about 0.3 wt. % or less, preferably no anionic polyacrylates.
12. Agent according to one of the points above which contains ethanol and/or isopropanol in a total amount of from about 0.5 to about 30 wt. %, preferably from about 3 to about 25 wt. %, particularly from about 7 to about 18 wt. %, as a percentage by weight relative to the liquid agent in each case.
13. Combination preparation (kit-of-parts) comprising the liquid agent according to one of points 1 to 12 as a component and an oxidant preparation as an additional component.
14. Combination preparation according to point 13, wherein the oxidant composition contains from about 1 to about 15 wt. %, preferably from about 3 to about 9 wt. %, particularly from about 4 to about 6 wt. % hydrogen peroxide (calculated as 100% $H_2O_2$) relative to the weight of the composition.
15. Combination preparation according to point 13 or 14, wherein the oxidant preparation contains at least one cationic surfactant selected from alkyltrimethylammonium chlorides, dialkyldimethylammonium chlorides and trialkylmethylammonium chlorides, in particular cetyl trimethyl ammonium chloride, stearyltrimethylammonium chloride, distearyldiemthylammonium chloride, lauryldimethylammonium chloride, lauryldimethylbenzylammonium chloride and tricetylmethylammonium chloride, and imidazolium compounds having the INCI names quaternium-27 and quaternium-83, preferably stearyltrimethylammonium chloride, wherein the at least one cationic surfactant is preferably contained in a total amount of from about 0.1 to about 4 wt. % relative to the total weight of oxidant preparation.
16. Combination preparation according to point 14 or 15, wherein the oxidant preparation contains about 0.3 wt. % or less, preferably no anionic polyacrylates.
17. Method for changing color of keratinous fibers comprising the following method steps: mixture of an agent according to one of points 1 to 12 with an oxidant preparation which, relative to its weight, preferably contains from about 1 to about 15 wt. %, more preferably from about 3 to about 8 wt. %, particularly from about 4 to about 6 wt. % hydrogen peroxide (calculated as 100% $H_2O_2$) and also preferably contains at least one cationic surfactant which is selected from alkyltrimethylammonium chlorides, dialkyldimethylammonium chlorides and trialkylmethylammonium chlorides, in particular cetyl trimethyl ammonium chloride, stearyltrimethylammonium chloride, distearyldimethylammonium chloride, lauryldimethylammonium chloride, lauryldimethylbenzylammonium chloride and tricetylmethylammonium chloride, and imidazolium compounds having the INCI names quaternium-27 and quaternium-83, particularly preferably from stearyltrimethylammonium chloride, most preferably in a total amount of from about 0.1 to about 4 wt. % relative to the weight of the oxidant preparation, followed by immediate application of the application mixture on the fibers, allowing the mixture to take effect for from about 5 to about 60 minutes and rinsing out of the application mixture and drying the hair, if applicable.

18. Method according to point 17, wherein the liquid agent according to one of points 1 to 12 and the oxidant composition is mixed in a weight ratio of from about 1:1 to about 1:3.

19. Method according to point 17 or 18, wherein the application mixture has a viscosity of from about 4500 to about 6100 mPa s (20° C., measured with a Haake rotational viscosimeter VT550, 20° C., rotation frequency: 8 rpm, rotary measuring system MVII).

The exemplary agent for oxidative dyeing of keratinous fibers, particularly human hair, is liquid before mixing with the oxidant preparation. The term liquid is understood to mean that the agent has a viscosity of from about 0.1 to about 200 mPa s, preferably from about 0.5 to about 100 mPa s, (measured with the Haake rotational viscosimeter VT550, 20° C. rotation frequency 8 rpm, rotary measuring system MVII). The exemplary agent for oxidative dyeing of keratinous fibers is also referred to hereinafter as a liquid hair dye or simply as "the liquid agent".

As contemplated herein, the term keratinous fibers comprises fur, wool and feathers, particularly human hair.

The liquid agent of the present disclosure contains, as component (a), at least one fatty acid that is liquid at 20° C. with from about 16 to about 22 carbon atoms in a total amount of from about 0.1 to about 15 wt. %, preferably from about 2 to about 12 wt. %, more preferably from about 5 to about 10 wt. % relative to the total weight of the liquid agent, wherein at least one part of the fatty acid is present in the form of a soap.

As contemplated herein, preference is given to fatty acids that are liquid at 20° C. selected from monovalent or multivalent unsaturated linear $C_{16}$-$C_{22}$ fatty acids and branched $C_{16}$-$C_{22}$ fatty acids selected, in particular from palmitoleic acid, oleic acid, linoleic acid, linolenic acid, arachidonic acid, 2-hexyldecanoic acid and isostearic acid, and mixtures of these fatty acids. As contemplated herein, oleic acid is particularly preferred.

The liquid agent as contemplated herein contains at least one alkanolamine selected from monoethanolamine, 2-amino-2-methylpropanol and triethanolamine as component (b) for transformation of the fatty acids in soaps and as an alkalizing agent. Preference is give to monoethanolamine. The alkanolamine is generally contained in the liquid agent in such an amount that at least a part of the fatty acid, preferably largely the whole or the whole fatty acid is present in the form of a soap. The alkanolamine is preferably contained in the exemplary liquid agent in a total amount of from about 1 to about 15 wt. %, more preferably from about 3 to about 12 wt. %, most preferably from about 5 to about 10 wt. % relative to the weight of the exemplary liquid agent in each case.

As contemplated herein, it is preferred that the alkanolamine is contained in the liquid agent as a general alkalizing agent. However, as contemplated herein, preference is also given to embodiments in which an additional alkalizing agent, such as alkalihydroxide and alkali carbonate, is contained. However, these are preferably contained in a low amount, particularly in a total amount of from about 0.01 to about 0.8 wt. %. In particular, it is preferred that about 0.8 wt. % or less, preferably about 0.4 wt. % or less, more preferably no ammoniac is contained hi the exemplary liquid hair dye as a weight percentage relative to the liquid hair coloring agent. In this manner, the negative properties of the ammonia, particularly its unpleasant odor, can be reduced or prevented altogether and, surprisingly, very good coloring results which are comparable to or even better than those of cream-like coloring agents were achieved. The examples of the present disclosure, in particular, demonstrate that, surprisingly, outstanding coloring results are also achieved without any ammonia at all.

The exemplary liquid hair dye contains, as an additional component, at least one oil component that is different from acid (a) in a total amount of from about 0.05 to about 5 wt. %, preferably from about 0.2 to about 3 wt. %, more preferably from about 0.5 to about 1.5 wt. % relative to the weight of the exemplary liquid hair coloring agent. The oil component is contained as a nourishing component that contributes to the nourishment provided by the exemplary liquid hair dyes and with which the coloring achieved with the oil component becomes more intensive. The oil component is preferably a liquid oil at 20° C. The exemplary liquid agent preferably contains fatty substances that are solid at 20° C. in a maximum total amount of about 0.3 wt. % or less, relative to the weight of the exemplary preferred agent. It is particularly preferred that no fatty substances that are solid at 20° C. are contained.

The solid substances that are solid at temperatures of about 20° C. or higher and are only contained in a maximum total amount of about 0.3 wt. % or less, relative to the weight of the agent preferred as contemplated herein, preferably not contained at all, include, for example, coconut fatty acid glycerol mono-, di- and triesters, butyrospermum parkii (shea butter), esters of saturated monohydric $C_8$-$C_{18}$ alcohols having saturated $C_{12}$-$C_{18}$ monocarboxylic acids, such as, for example, stearyl laurate, cetearyl stearate, cetyl pamitate and myristyl myristate, furthermore linear saturated alkanols having from about 12 to about 30 carbon atoms, in particular with from about 16 to about 22 carbon atoms, in particular cetyl alcohol, stearyl alcohol, arachidyl alcohol, behenyl alcohol and lanolin alcohol or mixtures of these alcohols, as they are available in the technical hydration of plant and animal fatty acids, as well as esters and particularly partial esters from a polyol having from about 2 to about 6 carbon atoms and linear saturated fatty acids having from about 12 to about 30 carbon atoms which can be hydroxylated. Such esters or partial esters are, for example, the mono- and diesters of glycerin or ethylene glycol or the monoesters of propylene glycol with linear saturated $C_{12}$-$C_{30}$ carboxylic acids which can be bydroxylated, particularly such with palmitic- and stearic acid, sorbrtanmono-, -di- or -triesters of linear saturated $C_{12}$-$C_{30}$ carboxylic acids which can be hydroxylated, such as those of myric acid, palmitic acid, stearic acid or of mixtures of these fatty acids, pentaerythritylmono-, -di-, tri- and -tetraesters and the methylglucose mono- and diesters of linear saturated $C_{12}$-$C_{30}$ carboxylic acids which can be hydroxylated, such as mono-, di-, tri- and tetraesters of pentaerythrite with linear saturated fatty acids having from about 12 to about 30 carbon atoms which can be hydroxylated, as well as esters from a saturated monovalent $C_{16}$-$C_{60}$ alkanol and a saturated $C_8$-$C_{36}$ monocarboxylic acid, such as cetyl behenate, stearyl behenate and $C_{20}$-$C_{40}$ alkyl stearate, glycerin triesters of saturated linear $C_{12}$-$C_{30}$ carboxylic acids which can be hydroxylated hardened castor oil, candelilla wax, carnauba wax, beeswax, saturated linear $C_{14}$-$C_{36}$ carboxylic acids and mixtures of the aforementioned substances.

As contemplated herein, particular preference is given to oils which are liquid at 20° C. selected from the esters of linear or branched saturated or unsaturated fatty alcohols with from about 2 to about 30 carbon atoms having linear or branched saturated or unsaturated fatty alcohols having from about 2 to about 30 carbon atoms which can be hydroxylated. This includes cetyl-2-ethylhexanoate e.g. Scherc-emol® CO ester), 2-hexyldecylstearate (e.g. Eutanol® G 16 S), 2-hexyldecyllaurate, isodecylneopentanoate, isononylisononanoate, 2-ethylhexylpalmitate (e.g. Cegesoft® C 24) and 2-ethylhexylstearate (e.g. Cetiol® 868). Preference is also given to isopropylmyristate, isopropylpalmitate, isopropylstearate, isopropyhsostearate, isopropyloleate, isooctylstearate, isononylstearate, isocetylstearate, isononylisononanoate, isotridecylisononanoate, cetearylisononanoate, 2-ethylhexyllaurate, 2-ethylhexylisostearate, 2-ethylhexylcocoate, 2-octyldodecylpalmitate, butyloctanoic acid-2-butyloctanoate, diisotridecylacetate, n-butylstearate, n-hexyllaurate, n-decyloleate, oleyloleate, oleylerucate, erucyloleate, erucylerucate, ethylene glycoldioleate and ethylene glycoldipalmitate. Particular preference is given to cetyl-2-ethylhexanoate. Very good nurturing effects were achieved as contemplated herein.

Additional oils preferred according to the present disclosure are selected from natural and synthetic hydrocarbons, particularly mineral oils, paraffin oils, C18-C30 isoparaffins, particularly isoeicosane, polyisobutene and polydecene, which are available, for example under the name Emery® 3004, 3006, 3010 or under the name Ethylflo® from Albemarle or Nexbase® 2004G from Nestlé, also selected from C8-C16 isoparaffins, particularly isodecane, isododecane, isotetradecane and isohexadecane, as well as mixtures thereof, as well as 1,3-di-(2-ethylhexyl)-cyclohexane (commercially available, for example, under the name Cetiol® S from BASF).

Additional oils preferred according to the present disclosure are selected from the benzoic acid, esters of linear or branched C8-22-alkanols. Particular preference is given to benzoic acid-$C_{12}$-$C_{15}$-alkyl esters, e.g. available as the commercial product Finsolv® TN, benzoic acid isostearyl esters, e.g. available as the commercial product Finsolv® SB, ethylhexylbenzoate, e.g. available as the commercial product Finsolv® EB, and benzoic acid octyldocecyl esters, e.g. available as the commercial product Finsolv® BOD.

Additional cosmetic oils preferred according to the present disclosure are selected from the triglycerides (=triple esters of glycerin) of linear or branched, saturated or unsaturated, if applicable hydroxylated C8-30 fatty acids, if they are liquid at 20° C. Particular preference is given to the use of natural oils, such as amaranthus seed oil, apricot kernel oil, arganil, avocado oil, babassu oil, cotton seed oil, borage oil, camel oil, safflower oil, peanut oil, grenadine core oil, grapefruit seed oil, hemp oil, hazelnut oil, hollowseed oil, currant seed oil, jojoba oil, linseed oil, macadamia nut oil, corn oil, almond oil, marula oil, evening primrose oil, olive oil, palm oil, palm kernel oil, parannut oil, pectic oil, peach kernel oil, rapeseed oil, castor oil, sandalwood oil, sanddornkernel oil, sesame oil, soya oil, sunflower oil, grapeseed oil, walnut oil, wild-type oil, wheat germ oil, and the liquid fractions of coconut oil and the like. However, preference is also given to synthetic triglyceride oils, particularly capric/caprylic triglycerides, i.e. the commercial product Myritol® 318 (BASF) having unbranched fatty acid esters and glyceryl triisostearin with branched fatty acids.

Additional particularly preferred cosmetic oils according to the present disclosure are selected from the dicaxboxylic acid esters of linear or branched $C_2$-$C_{10}$ alkanols, particularly diisopropyl adipate, di-n-butyl adipate, di (2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Additional preferred cosmetic oils according to the present disclosure are selected from the adducts of from about 1 to about 5 propylene oxide units on mono- or multivalent C8-22 alkanols, such as octauol, decanol, decanediol, lauryl alcohol, myristyl alcohol and stearyl alcohol, e.g. PPG-2 myristyl ether and PPG-3 myristyl ether (e.g. Witconol® APM).

Additional preferred cosmetic oils according to the present disclosure are selected from the adducts of at least about 6 ethylene oxide and/or propylene oxide units on mono- or multivalent C3-22 alkanois, such as glycerin, butanol, butanediol, myristyl alcohol and stearyl alcohol which can be optionally esterified, such as PPG-14 butyl ether (e.g. Ucon Fluid® AP), PPG-9 butyl ether (e.g. Breox® B25), PPG-10 butanediol (e.g. Macol® 57), PPG-15 stearyl ether (e.g. Arlamol® E) and glycereth-7-diisononanoate.

Additional preferred cosmetic oils according to the present disclosure are selected from the $C_8$-$C_{22}$ fatty alcohol esters of monovalent or multivalent $C_2$-$C_7$ hydroxy carboxylic acids, particularly the esters of glycolic acid, lactic acid, malic acid, tartaric acid, citric acid and salicylic acid. Such esters based on linear C14/15 alkanols, such as $C_{12}$-$C_{15}$ alkyl lactate, and on C12/13 alkanols branched in 2-position are commercially available under the trade name Cosmacol® from Nordmann Rassmann GmbH & Col, Hamburg, particularly the commercial products Cosmacol® ESI, Cosmacol® EMI and Cosmacol® ETI.

Additional preferred cosmetic oils according to the present disclosure are selected from the symmetrical, asymmetrical or cyclical esters of carboxylic acid with $C_{3-22}$ alkanols, $C_{3-22}$ alkanediols or $C_{3-22}$ alkanetriols, e.g. dicaprylylcarbonate (Cetiol® CC) or the esters according to the teaching of DE 19756454 A1, particularly glycerin carbonate.

Additional cosmetic oils that cars be preferred according to the present disclosure are selected from the esters of dimeric unsaturated $C_{12}$-$C_{22}$ fatty acids (dimeric fatty acids) with monovalent linear, branched or cyclical $C_2$-$C_{18}$ alkanols or multivalent linear and branched $C_2$-$C_6$ alkanols.

Additional cosmetic oils that are suitable according to the present disclosure are selected from the silicone oils, which include, for example, dialkyl- and akylaryl siloxanes, such as cyclopentadienyl, cyclohexsiloxane, dimethylpolysiloxane and methylphenylpolysiloxane, but also hexamethyldisiloxane, octamethyltrisiloxane and decamethyltetrasiloxane. Preference can be given to volatile silicone oils which can be cyclic, such as octamethylcyclotetrasiloxane, decamethylcyclopentasiloxane and dodecamethylcyclohexsiloxane, and mixtures thereof, as are contained, for example, in the commercial products DC 244, 245, 344 and 345 of Dow Corning. Volatile silicone oils are also suitable, particularly hexamethyldisiloxane (L2), octamethyltrisiloxane (L3), Decamethyltetrasiloxan (L4) and any double and trouble mixtures of L2, L3 and/or L4, preferable such mixtures which are commercially available, for example, in the products DC 2-1184, Dow Corning® 200 (0.65 cSt) and Dow Corning® (1.5 cSt) from Dow Corning. Preferred nonvolatile silicone oils are selected from higher molecular linear dimethylpolysiloxanes, commercially available, for example, under the name Dow Corning® 190, Dow Corning® 2000 Fluid with kinematic viscosities (25° C.) in a range of from about 5 to about 100 cSt, preferably from about 5 to about 50 cSt or also from about 5 to about 10 cSt, and dimethylpolysiloxane with a kinematic viscosity (25° C.) of approximately 350 cSt.

As contemplated herein, preference can be given to use of mixtures of the aforementioned oils.

As contemplated herein, no fatty alcohols that are branched and have about 7 or more carbon atoms are contained in the liquid agent. Furthermore, as contemplated herein, preference is given to fatty alcohols not included in the liquid agent which have a melting point of about 25° C. or higher. The branched fatty alcohols that are not included in the liquid hair dye according to the present disclosure include, for example, Guerbert alcohols such as octyldecanol, octyldodecanol, isocetyl alcohol and isostearyl alcohol.

The fatty alcohols that have a melting point of about 25° C. or higher and are not included in the liquid hair dye as contemplated herein, include, for example, linear saturated fatty alcohols with about 14 or more carbon atoms, such as myristyl alcohol, cetyl alcohol and stearyl alcohol.

However, embodiments as contemplated herein can contain other fatty alcohols and/or alkanols in the liquid hair dye. For example, linear, saturated or unsaturated fatty alcohols with about 7 or more, for example from about 7 to about 24 carbon atoms, are included, if they have a melting point below about 25° C. Linear saturated fatty alcohols that can be included in this liquid agent in embodiments as contemplated herein are, in particular, $C_2$ to $C_{12}$ fatty alcohols, such as 1-heptanol, 1-octanol, 1-nonanol, 1-decanol, 1-undecanol and/or 1-dodecanol. Linear unsaturated fatty alcohols that can be contained in the liquid hair dye are, for example, oleyl alcohol and/or linoleyl alcohol.

Furthermore, branched alkanols that contain less than about 7 carbons atoms, such as t-butanol or hexylene glycol (−2-methyl-2,4-pentanediol) can be included in embodiments of the present disclosure.

The fatty alcohols or alkanols optionally included in the liquid dye can have up to about 4 hydroxy groups.

The presence of at least one alkylamidoamine as component (d) is essential for the present disclosure in a total amount of from about 0.05 to about 6 wt. % in the liquid hair dye, relative to the total weight of the liquid hair dye. The at least one alkylamidoamine is preferably contained in a total amount of from about 0.1 to about 3 wt. %, more preferably from about 0.1 to about 2 wt. %, even more preferably from about 0.2 to about 1 wt. %, and particularly from about 0.2 to about 0.6 wt. %. The alkylamidoamine is preferably selected from stearamidopropyl dimethylamine (e. g. Adogen® S18 V or Tego® Amid S 18 or Incromine® SB), cocarnidopropyl dimethylamine (e. g. Mackine® 101), ricinoleic amidopropyl dimethylamine (e. g. Mackine® 201), isostearamidopropyl dimethylamine (e. g. Mackine® 401), olearnidopropyl dimethylamine (e. g. Mackine® 501), behenarnidopropyl dimethylamine (e. g. Mackine® 601, Incromine® BD), palmamidopropyl dimethylamine, quaternium-33, (e. g. Swanol® Lanoquat DES-50), behenamidopropyl ethyldimonium ethosulfate e. g. Schercoquat® BAS) and combinations thereof, and is preferably stearamidopropyl diemthylamine, in particular. Quaternium-33, behamidopropyl ethyldimenium ethosulfate are permanently cationic alkylamidoamines, which are likewise encompassed by the term amidoamine as contemplated herein. Alkylamidoamines are regarded as one of a plurality of constituents of hair-conditioning agents, agents for improving the washing resistance of already dyed hair and also in hair dye shampoos in WO 2015/090805 A1. However, it was surprising that the use of an alkylamidoamine in liquid oxidation hair dyes, i.e. in coloring agents of two-component hair coloring systems, led to significantly improved staining intensities compared to known, viscous oil-containing coloring agents.

Furthermore, the exemplary liquid hair dye contains at least one oxidation dye precursor. As contemplated herein, there are basically no limitations with respect to the oxidant dye precursors. Oxidative coloring agents contain so-called developers and coupler components for the formation and coloring. Developers find couplers diffuse separately in the keratinous fibers and produce the actual dyes under the influence of an alkalizing agent and an oxidant (typically hydrogen peroxide) in chemical reaction with each other. Depending on the amount of oxidant which is used, the keratinous fibers are lightened to a varying degree, because the oxidant initiates the dye formation process of developers find couplers and simultaneously destroys the hair's own pigment (melanine) oxidatively. Depending on the use amounts of the oxidation dye precursors and of the oxidant, the oxidative coloration can therefore primarily be a coloration (with a high dye content) or primarily a brightening (with a high proportion of oxidant). In the latter case, the oxidant dye precursors are primarily used for the nuancing of the lightening result.

Oxidation dye precursors used according to the present disclosure include oxidation dye precursors of the developer and coupler types. Particularly suitable oxidation dye precursors of the developer type are selected from at least one compound from the group consisting of p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis(2-hydroxyethyl)-N,N'-bis(4-aminophenyl)-1,3-diamino-propane-2-ol, bis-(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-aminophenol, 4-amino-3-methyphenol, 4-amino-2-aminomethylphenol, 4-amino-2-(1,2-dihydroxyethyl)phenol, 4-amino-2-(diethylaminomethyl) phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, 2,3-diamino-6,7-dihydro-1H, 5H-pyrazolo[1,2-a]pyrazol-1-one and the physiologically tolerate salts thereof.

Particularly suitable oxidation dye precursors of the coupler type are selected from the group consisting of 3-aminophenol, 5-amino-2-methylphenol, 3-amino-2-chloro-6-methylphenol, 2-hydroxy-4-aminophenoxyethanol, 5-amino-4-chlor-2-methyphenol, 5-(2-hydroxyethyl)-amino-2-methylphenol, 2,4-dichlor-3-aminophenol, 2-aminophenol, 3-phenylendiamine, 2-(2,4-diaminophenoxy)ethanol, 1,3-bis(2,4-diaminophenoxy)propane, 1-methoxy-2-amino-4-(2-hydroxyethylamino)benzol, 1,3-bis(2,4-diaminophenyl)propane, 2,6-bis(2'-hydroxyethylamino)-1-methylbenzol, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzol, resorcin, 2-methylresorcin, 4-chlorresorcin, 1,2,4-trihydroxybenzol, 2-amino-3-hydroxypyridin, 3-amino-2-methylamino-6-methoxypyridin, 2,6-dihydroxy-3,4-dimethylpyridin, 3,5-diamino-2,6-dimethoxypyridin, 1-phenyl-3-methylpyrazol-5-on, 1-naphthol, 1,5-dihydroxynaphthalin, 2,7-dihydroxynaphthalin, 1,7-dihydroxynaphthalin, 1,8-dihydroxynaphthalin, 4-hydroxyindol, 6-hydroxyindol, 7-hydroxyindol, 4-hydroxyindolin, 6-hydroxyindolin, 7-hydroxyindolin or mixtures of said compounds or the physiologically compatible salts thereof.

In a preferred embodiment, the exemplary liquid hair dyes contain the at least one oxidation dye precursor in a total amount of from about 0.1 to about 12.0 wt. %, preferably from about 0.5 to about 10.0 wt. %, more preferably from about 1.0 to about 8.0 wt. % relative to the weight of the liquid hair dye.

In a further embodiment, the exemplary agents can also contain at least one partially-oxidizing dye. Partially-oxidizing dyes can be sub-divided into anionic, cationic acid non-ionic partially-oxidizing dyes. The partially-oxidizing dyes are preferably selected from the nitrophenylenediamines, the nitroaminophenols, the azo dyes, the anthraquinones, the triarylmethane dyes or the indophenols and the physiologically acceptable salts thereof. The additional partially-oxidizing dyes are preferably contained in a total amount of from about 0.001 to about 4 wt. % relative to the weight of the exemplary agent.

Preferred anionic partially-oxidizing dyes are the compounds known under the international designations and/or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromphenol blue and tetrabromphenol blue.

Preferred cationic partially-oxidizing dyes are cationic triphenylmethane dyes, such as Basic Blue 7, Basic Blue 26, Basic Violet 2 and Basic Violet 14, aromatic systems, which are substituted with a quarternary nitrogen group, such as Basic Yellow 57, Basic Red 76, Basic Blue 99, Basic Brown 16 and Basic Brown 17, cationic anthraquinone dyes, such as HC Blue 16 (Bluequat B), as well as partially-oxidizing dyes containing a heterocyclus, which as at least one quarternary nitrogen atom, more particularly Basic Yellow 87, Basic Orange 31 and Basic Red 51. The cationic partially-oxidizing dyes, which are sold under the trade name of Arianor, are also suitable cationic partially-oxidizing dyes as contemplated herein.

Suitable non-ionic substantive dyes are, in particular, non-ionic nitro and quinone dyes and neutral azo dyes. Preferred nonionic partially-oxidizing coloring agents are the compounds known under the international designations and/or trade name HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzol, 2-amino-4-nitrophenol, 1,4-bis-(2-hydroxyethyl)-amino-2-nitrobenzol, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzol, 1-amino-4-(2-hydroxyethyl)amino-5-chlor-2-nitrobenzol, 4-amino-3-nitrophenol, 1-(2'-Ureidoethyl)amino-4-nitrobenzol, 2-[(4-amino-2-nitrophenyl)amino]benzoic acid, 4-[(3-hydroxypropyl)amino]-3-nitrophenol, 4-nitro-o-phenylendiamine, 6-nitro-1,2,3,4-tetrahydrochinoxaline, 2-hyroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol are particularly preferred.

The exemplary liquid agents contain the essential components for the present disclosure in a hydrous cosmetic carrier, preferably in a hydrous-alcoholic carrier, wherein ethanol and/or isopropanol is/are preferred as alcohol. The liquid agent preferably contains ethanol and/or isopropanol in a total amount of from about 0.5 to about 30 wt. %, preferably from about 3 to about 25 wt. %, particularly from about 7 to about 18 wt. %, as a percentage by weight relative to the liquid agent in each case. Particular preference is given to ethanol an in an amount of from about 0.5 to about 30 wt. %, preferably from about 3 to about 25 wt. %, particularly from about 7 to about 18 wt. %, as a percentage by weight relative to the liquid agent in each case.

In preferred embodiments of the present disclosure, the liquid hair dye can contain an additional anionic surfactant which is different from the soap, at least one nonionic surfactant or a mixture thereof. Particularly preferred embodiments of the present disclosure, the liquid hair agent does not contain any anionic surfactants except for the fatty acid in the form of a soap. In cases in which no additional anionic surfactant is contained in addition to the fatty acid in the form of a soap, the liquid hair coloring agent preferably contains at least one nonionic surfactant. In another, likewise preferred embodiment, the liquid hair coloring agent contains an additional anionic surfactant and at least one nonionic surfactant in addition to the fatty acid in the form of a soap.

In principle, all anionic surfactant substances which are suitable for use on the human body are suitable as additional anionic surfactants. They are exemplified by an water-solubilizing anionic group, such as a carboxylate, sulfate or sulfate group, sulfonate or phosphate group and a lipophilic alkyl group having from about 8 to about 30 carbon atoms. Furthermore, the molecule can contain glycol or polyglycol ether groups, ester, ether and amide groups, as well as hydroxyl groups. The additional anionic surfactants are present in the form of sodium, potassium and ammonium salts, as well as mono-, di- and trialkanol ammonium salts having from about 2 to about 4 carbon atoms in the alkanol group, Additional preferred anionic surfactants are selected from linear alkyl sulfates having from about 8 to about 24 carbon atoms, ethylene oxide adducts thereof and combinations thereof. Preference is given to linear alkyl sulfates and-or ethylene oxide adducts of linear alkyl sulfates (alkyl ether sulfates). It is particularly preferred that the additional anionic surfactant is an alkyl sulfate having from about 10 to about 18 carbon atoms, preferably from about 12 to about 14 carbons, and/or an alkyl ether sulfate having from about 10 to about 18 carbon atoms, preferably from about 12 to about 14 carbon atoms, having from about 1 to about 6 ethylene oxide units, more preferably from about 2 to about 4 ethylene oxide units. Particular preference is given to lauryl sulfate, particularly sodium lauryl sulfate and/or a lauryl ether sulfate having from about 2 to about 4 ethylene oxide units. Particular preference is given to a combination of lauryl sulfate, particularly sodium lauryl sulfate and lauryl ether sulfate, particularly sodium lauryl ether sulfate.

The exemplary liquid hair dye preferably contains the additional anionic surfactant in a total amount of approximately 0.1 to about 3 wt. %, more preferably from about 0.2 to about 2 wt. %. particularly from about 0.5 to about 1.5 wt. % relative to the total weight of the liquid hair dye.

In principle, all nonionic surfactant substances which are suitable for use on the human body are suitable nonionic surfactants. As contemplated herein, the liquid hair dye contains an alkyl and/or alkenyl monoethanolamide having from about 8 to about 18 carbon atoms in the alkyl chain and/or alkenyl chain, and/or an adduct of from about 1 to about 5 mol of ethylene oxide, preferably from about 2 to about 4 mol of ethylene oxide as a nonionic surfactant on a fatty alcohol having from about 8 to about 22 carbon atoms, preferably from about 12 to about 14 carbon atoms, wherein the fatty alcohol is preferably linear. Preference is given to a combination of the alkyl and/or alkenyl monoethanolamides having from about 8 to about 18 carbon atoms in the alkyl chain and/or alkenyl chain, and/or an adduct of from about 1 to about 5 mol of ethylene oxide, preferably from about 2 to about 4 mol of ethylene oxide on a fatty alcohol having from about 8 to about 22 carbon atoms, preferably from about 12 to about 14 carbon atoms. Particular preference is given to alkyl or alkenyl monoethanolamide selected from lauric acid monoethanolamide (INCI: lauramide MEA), coconut oil fatty acid monoethanolamide (INCI: cocamide MEA) and combinations thereof. The adducts of from about 1 to about 5 mol of ethylene oxide, preferably from about 2 to about 4 mole of ethylene oxide, on a fatty alcohol having from about 8 to about 22 carbon atoms are preferably selected from ethylene oxide adducts of lauryl alcohol, particularly Laureth-2 (INCI). As contemplated herein, however, preference is also given to the use of ethylene oxide adducts having from about 1 to about 5 mole of ethylene oxide, preferably from about 2 to about 4 mole of ethylene oxide, on cetyl alcohol, myristyl alcohol, stearyl alcohol, palmitoleyl alcohol or oleyl alcohol. The at least on nonionic surfactant is preferably contained in a total amount of from about 5 to about 20 wt. %, more preferably from about 5 to about 15 wt. %, as well as from about 8 to about 12 wt. %, relative to the liquid hair coloring agent.

If a combination of the alkyl and/or alkenyl monoethanolamides having from about 8 to about 18 carbon atoms in the alkyl chain and the adduct of from about 1 to about 5 mol of ethylene oxide, preferably from about 2 to about 4 mol of ethylene oxide is contained as a nonionic surfactant on a fatty alcohol having from about 8 to about 22 carbon atoms, preferably from about 12 to about 14 carbon atoms, it is preferably present in the following percentages. The alkyl and/or alkenyl monoethanolamide having from about 8 to about 18 carbon atoms in the alkyl chain or alkenyl chain is preferably present in the liquid agent in a total amount of from about 0.5 to about 5 wt. %, likewise preferably from about 1 to about 4 wt. %, more preferably from about 1 to about 3 wt. %, relative to the total amount of the liquid agent, and the adduct of from about 1 to about 5 mol of ethylene oxide, preferably from about 2 to about 4 mol of ethylene oxide, on a fatty alcohol having from about 8 to about 22 carbon atoms, preferably from about 12 to about 14 carbon atoms in a total amount of from about 5 to about 15 wt. %, likewise preferably from about 7 to about 12 wt. %, more preferably from about 8 to about 10 wt. %, relative to the total amount of the liquid agent.

In preferred embodiments of the present disclosure, the liquid oxidation hair dye is not in the form of an emulsion. In this case, the oils contained in the liquid agent are dissolved, e.g. in an ethanol or isopropanol. The oils can also be present in a solubilized form with a high portion of surfactants as micelles, winch can have a diameter small enough that optical light is not scattered. In both cases, a clear and liquid composition is present.

In another preferred embodiment of the present disclosure, the liquid oxidation hair dye has a turbidity of from about 0.1 to about 150 NTU (nephelometric turbidity units, preferably from about 5 to about 100 NTU, particularly preferably from about 10 to about 80 NTU, measured in each case according to ISO 7027 in the version of 1999, preferably measured at 20° C.

Agents for oxidative dyeing of keratinous fibers, particularly such that are present in a cream-like form, frequently contain anionic polymers such as acrylates as thickening agents, i.e. salts of polyacrylic acids which can be copolymerized with other polyacrylic acid derivatives, such as polyacrylic acid esters or polyacrylamides. In the present disclosure, it is preferred that the liquid hair coloring agent contains only about 0.3 wt. % or less, preferably no anionic polymers, particularly anionic polyacrylates.

Dyeing and lightening processes on keratinous fibers usually occur in an alkali environment. To protect the keratinous fibers and also the skin as much as possible, setting too high a pH value is however not desirable. Therefore, it is preferred that the pH value of the exemplary liquid agent is in the range of from about 6 to about 12, more preferably in the range of from about 7 to about 11, particularly in the range of from about 8 to about 10.5, The pH values according to the present disclosure are pH values that were measured at a temperature of 20° C.

The exemplary agents are liquid agents for oxidative dyeing of hair. The exemplary liquid agents contain from about zero to a maximum of about 0.2 wt. % of oxidant, preferably about zero wt. % of oxidant.

The exemplary preferred liquid agent/liquid hair coloring agent is mixed with the oxidant preparation before use in order to obtain an application mixture. The oxidation dye precursors react with the oxidant to form the actual dyes in the application mixture and/or on the hair. The exemplary agents, therefore, are normally marketed as a multicomponent kit, usually as a two-component kit. The first component is the exemplary liquid hair dye described in detail above (Preparation A), which is mixed shortly before use with the oxidant preparation (Preparation B).

Therefore, the present disclosure relates to a combination preparation (kit-of-parts), comprising the liquid agent (liquid hair dye) as one component as contemplated herein and an oxidant preparation as an additional component.

The oxidant composition contains from about 1 to about 15 wt. %, preferably from about 3 to about 8 wt. %, particularly from about 4 to about 6 wt. % hydrogen peroxide (calculated as 100% $H_2O_2$) relative to the weight of the composition.

It is particularly preferred that the oxidant preparation contains at least one cationic surfactant which is selected from alkyltrimethylammonium chlorides, dialkyldimethylammonium chlorides and trialkylmethylammonium chlorides, in particular cetyl trimethyl ammonium chloride, stearyltrimethylammonium chloride, distearyldimethylammonium chloride, lauryldimethylammonium chloride, lauryldimethylbenzylammonium chloride and tricetylmethylammonium chloride, and imidazolium compounds having the INCI designations Quaternium-27 and Quaternium-83, and particularly preferably stearyltrimethylammonium chloride, wherein the at least one cationic surfactant, in particular stearyltrimethylammonium chloride, preferably in a total amount of from about 0.1 to about 4 wt. % in the oxidant preparation, more preferably from about 0.1 to about 2 wt. % in the oxidant preparation, even more preferably from about 0.2 to about 0.6 wt. %, relative the total weight of the oxidant preparation.

This oxidant preparation can contain additional normal components of oxidant preparations, such as care components, like the chelating agents and preservative components indicated above for the liquid hair coloring agent. For example, oils/care components can be contained in a total amount of from about 0.1 to about 10 or from about 0.2 to about 5 wt. % relative to the oxidant composition.

The liquid agent of the present disclosure also preferably contains the oxidant preparation in only about 0.3 wt. % or less, preferably no anionic polymers, particularly anionic polyacrylates.

Surprisingly, in the presence of the cationic surfactant, in particular, it was found that the liquid hair coloring agent forms a gen after mixing the oxidant preparation, which has a suitable viscosity for application. The viscosity of the application mixture should be adjusted so that the application mixture remains thin enough in order to optimally wet the keratinous fibers and to adequately ensure rapid diffusion of oxidants and/or dye precursors into the keratinous fibers, while at the same time not being so thin that the application formulation drips from, the keratinous fibers. According to the present disclosure the viscosity of the application mixture is preferably present in the range of from about 4100 to about 6500 mPa s (20° C., measured with the Haake rotation viscosimeter VT550, 20° C., rotation frequency: 8 rpm, rotary measuring system MVII).

In particular in the presence of the cationic surfactant in the oxidizing agent preparation, it was surprisingly found that, in combination with the liquid hair color of the present disclosure, which as necessary constituent, is an alkylamidoamine, preferably stearylamidopropyl dimethylamine, an excellent coloring performance could be achieved.

As contemplated herein, the liquid hair coloring agent and the oxidant preparation are preferable mixed together in a weight ratio (liquid hair dye: oxidant preparation) of from about 1:3 to about 3:1, preferably from about 1:1 to about 1:3, particularly from about 1:1 to about 1:2, in order to obtain the application mixture.

The present disclosure also relates to a method for changing the color of keratinous fibers, comprising the following method steps: mixing a liquid agent according to the present disclosure with an oxidant preparation, which, relative to its weight, preferably contains from about 1 to about 15 wt. %, more preferably from about 3 to about 8 wt. %, particularly from about 4 to about 6 wt. %, hydrogen peroxide (calculated as 100%, $H_2O_2$), followed directly by application of the application mixture on the fibers, leaving the mixture in place to take effect for from about 5 to about 60 minutes and rinsing off the application mixture and, optionally, drying the hair. Furthermore, it is preferred that the oxidant preparation contains at least one canonic surfactant which is selected from alkyltrimethylammonium chlorides, dialkyldimethylammonium chlorides and trialkylmethylammonium chlorides, in particular cetyl trimethyl ammonium chloride, stearyltrimethylammonium chloride, distearyldimethylammonium chloride, lauryldimethylammonium chloride, lauryldimethylbenzylammonium chloride and tricetylmethylammonium chloride, and imidazolium compounds having the INCI designations Quaternium-27 and Quaternium-83, particularly preferably stearyltrimethylammonium chloride, wherein the at least one cationic surfactant, in particular stearyltrimethylammonium chloride, preferably m a total amount of from about 0.1 to about 4 wt. % in the oxidant preparation, more preferably from about 0.1 to about 2 wt. % in the oxidant preparation, even more preferably from about 0.2 to about 0.6 wt. %, relative the total weight of the oxidant preparation.

With respect to the preferred embodiments of the method, the same applies mutatis mutandis to the liquid agent and the oxidizing agent preparation.

Tabular Overview

The composition of some liquid hair dyes preferred according to the present disclosure can be found in fee table below (values in wt. % relative to the total weight of the cosmetic agent, unless otherwise stated).

| | Formula 1 | Formula 2 | Formula 3 | Formula 4 |
|---|---|---|---|---|
| Fatty acid which is liquid at 20° C. having 16 to 22 carbon atoms | 0.1 to 15 | 1 to 12 | 2 to 10 | 5 to 10 |
| Alkanolamine | 1 to 15 | 2 to 15 | 3 to 12 | 5 to 10 |
| Oil components | 0.05 to 5 | 0.1 to 4 | 0.2 to 3 | 0.5 to 2 |
| Alkylamidoamine | 0.05 to 6 | 0.1 to 3 | 0.2 to 2 | 0.2 to 0.6 |
| Misc | ad 100 | ad 100 | ad 100 | ad 100 |

| | Formula 1a | Formula 2a | Formula 3a | Formula 4a |
|---|---|---|---|---|
| Oleic acid | 0.1 to 15 | 1 to 12 | 2 to 10 | 5 to 10 |
| Monoethanolamine | 1 to 15 | 2 to 15 | 3 to 12 | 5 to 10 |
| Cetyl-2-ethylhexanoate | 0.05 to 5 | 0.1 to 4 | 0.2 to 3 | 0.5 to 2 |
| Stearamidopropyl dimethylamine | 0.05 to 6 | 0.1 to 3 | 0.2 to 2 | 0.2 to 0.6 |
| Misc | ad 100 | ad 100 | ad 100 | ad 100 |

| | Formula 5 | Formula 6 | Formula 7 | Formula 8 |
|---|---|---|---|---|
| Fatty acid which is liquid at 20° C. having 16 to 22 carbon atoms | 0.1 to 15 | 1 to 12 | 2 to 10 | 5 to 10 |
| Alkanolamine | 1 to 15 | 2 to 15 | 3 to 12 | 5 to 10 |
| Oil components | 0.05 to 5 | 0.1 to 4 | 0.2 to 3 | 0.5 to 2 |
| Alkylamidoamine | 0.05 to 6 | 0.1 to 3 | 0.2 to 2 | 0.2 to 0.6 |
| Nonionic surfactant | 5 to 20 | 5 to 15 | 5 to 10 | 5 to 10 |
| Misc | ad 100 | ad 100 | ad 100 | ad 100 |

| | Formula 5a | Formula 6a | Formula 7a | Formula 8a |
|---|---|---|---|---|
| Fatty acid which is liquid at 20° C. having 16 to 22 carbon atoms | 0.1 to 15 | 1 to 12 | 2 to 10 | 5 to 10 |
| Alkanolamine | 1 to 15 | 2 to 15 | 3 to 12 | 5 to 10 |
| Oil components | 0.05 to 5 | 0.1 to 4 | 0.2 to 3 | 0.5 to 2 |
| Alkylamidoamine | 0.05 to 6 | 0.1 to 3 | 0.2 to 2 | 0.2 to 0.6 |
| Nonionic surfactant: alkyl and/or alkenyl monoethanolamide having 8 to 18 carbon atoms in the alkyl chain | 0.5 to 5 | 1 to 4 | 1 to 3 | 1 to 3 |
| Nonionic surfactant: adduct of 1 to 5 mol of ethylene oxide on a linear fatty alcohol having 8 to 22 carbon atoms, preferably 12 to 14 carbon atoms | 5 to 15 | 7 to 12 | 8 to 10 | 8 to 10 |
| Misc | ad 100 | ad 100 | ad 100 | ad 100 |

| | Formula 5b | Formula 6b | Formula 7b | Formula 8b |
|---|---|---|---|---|
| Fatty add which is liquid at 20° C. having 16 to 22 carbon atoms | 0.1 to 15 | 1 to 12 | 2 to 10 | 5 to 10 |
| Alkanolamine | 1 to 15 | 2 to 15 | 3 to 12 | 5 to 10 |
| Oil components | 0.05 to 5 | 0.1 to 4 | 0.2 to 3 | 0.5 to 2 |
| Alkylamidoamine | 0.05 to 6 | 0.1 to 3 | 0.2 to 2 | 0.2 to 0.6 |
| Cocamide MEA and/or Lauramide MEA | 0.5 to 5 | 1 to 4 | 1 to 3 | 1 to 3 |
| Laureth-2 | 5 to 15 | 7 to 12 | 8 to 10 | 8 to 10 |
| Misc | ad 100 | ad 100 | ad 100 | ad 100 |

"Misc" is understood, in particular, to mean a hydrous cosmetic carrier, preferably a hydrous alcoholic cosmetic carrier, such as water/ethanol or water/isopropanol, where ethanol and/or isopropanol is preferably contained in a total amount of from about 0.5 to about 30 wt. %, preferably from about 3 to about 25 wt. %, particularly from about 7 to about 18 wt. % in the compositions. Misc can also include normal components of liquid coloring agents, such as chelating agents for heavy metal ions, preservatives, fragrances and/or perfumes.

"Misc" preferably does not contain any anionic polymers, such as anionic polyacrylates In preferred embodiments, "Misc" does not include any additional anionic surfactants except for the fatty acid in the form of a soap.

EXAMPLES

The coloring agents presented in Tables 1 and 2 below were produced. The quantity formulations indicate percent by weight, unless otherwise specified.

Compositions of hair coloring agents wherein the compositions 12 to 14 in Table 2 are exemplary (specifications in wt. %):

TABLE 1

| Component | 1 | 2 | 3 | 4 | 5 | 6 | 7 |
|---|---|---|---|---|---|---|---|
| Sodium Laureth Sulfate | 0.32 | 0.32 | 0.43 | 0.43 | 0.43 | 0.43 | 0.32 |
| Ammonium Lauryl Sulfate | 0.35 | 0.35 | 0.63 | 0.63 | 0.63 | 0.63 | 0.63 |
| Texapon ® K12G | — | — | — | — | — | — | — |
| Comperlan ® 100 | 1 | 1 | 2 | 2 | 2 | — | 2 |
| Disodium Cocoamphodiacetate | — | — | — | — | — | 1.25 | — |
| Stearamidopropyl dimethylamine | — | — | — | — | — | — | — |
| Dye precursors | 6.72 | 6.72 | 6.72 | 6.72 | 6.72 | 6.72 | 6.72 |
| Ethanol | 13 | 13 | 13 | 13 | 13 | 13 | 13 |
| Oleic acid | 7 | 7 | 7 | 7 | 7 | 7 | 7 |
| Dehydol ® LS2 Deo N | — | — | — | 5 | 6 | 8 | 8 |
| Eumulgin ® O 5 | 5 | — | 0.15 | — | — | — | — |
| Schercemol™ CO Ester | — | — | — | — | — | 1.5 | 1.5 |
| PPG5-Ceteth-20 | — | 4.5 | 5 | — | — | — | — |
| Polyethylene glycol MG 400 | — | — | — | — | 1.5 | — | — |
| Antil ® 200 | — | — | — | — | — | — | — |
| Monoethanolamine | 4.5 | 4.5 | 4.5 | 4.5 | 4.5 | 4.5 | 4.5 |
| Water | 3 | 3 | 3 | 3 | 3 | 3 | 3 |
| EDTA | 0.2 | 0.2 | 0.2 | 0.2 | 0.2 | 0.2 | 0.2 |
| Ascorbic acid | 0.3 | 0.3 | 0.3 | 0.3 | 0.3 | 0.3 | 0.3 |
| Monoethanol thio-glycolate | 0.05 | 0.05 | 0.05 | 0.05 | 0.05 | 0.05 | 0.05 |
| Water | ad 100 | ad 100 | ad 100 | ad 100 | ad 100 | ad 100 | ad 100 |
| Results | | | | | | | |
| Consistency Appearance | Gel | liquid turbid | liquid turbid | liquid clear | liquid clear | liquid clear | liquid clear |
| Consistency with developer | | not thick | not thick | not thick | not thick | not thick | some what thicker |

TABLE 2

| Component | 8 | 9 | 10 | 11 | 12* | 13* | 14* |
|---|---|---|---|---|---|---|---|
| Sodium Laureth Sulfate | 0.32 | 0.32 | 0.43 | 0.43 | 0.43 | 0.43 | — |
| Ammonium Lauryl Sulfate | 0.63 | 0.63 | — | — | — | — | — |
| Texapon ® K12G | — | — | 0.7 | 0.7 | 0.7 | 0.7 | — |
| Comperlan ® 100 | 2 | 2 | 2 | 2 | 2 | 2 | 2.2 |
| Disodium Cocoamphodiacetate | — | — | — | — | — | — | — |
| Stearamidopropyl dimethylamine | — | — | — | — | 0.4 | 0.5 | 0.5 |
| Dye precursors | 6.72 | 6.72 | 6.72 | 6.72 | 6.72 | 6.72 | 6.72 |
| Ethanol | 13 | 13 | 13 | 18 | 15 | 15 | 16 |
| Oleic acid | 7 | 7 | 7 | 6 | 7 | 7 | 7 |
| Dehydol ® LS2 Deo N | 8 | 8 | 9 | 10.5 | 9 | 9 | 9 |

TABLE 2-continued

|  | 8 | 9 | 10 | 11 | 12* | 13* | 14* |
|---|---|---|---|---|---|---|---|
| Eumulgin ® O 5 | — | — | — | — | — | — | — |
| Schercemol ™ CO Ester | — | — | 2 | 2 | 2 | 1 | 0.8 |
| PPG5-Ceteth-20 | — | — | — | — | — | — | — |
| Polyethylene glycol MG 400 | 1.5 | — | — | — | — | — | — |
| Antil ® 200 | — | 0.5 | — | — | — | — | — |
| Monoethanolamine | 4.5 | 4.5 | 6 | 6 | 6 | 6.5 | 8 |
| Water | 3 | 3 | 3 | 3 | 3 | 3 | 3 |
| EDTA | 0.2 | 0.2 | 0.2 | 0.2 | 0.2 | 0.2 | 0.2 |
| Ascorbic acid | 0.3 | 0.3 | 0.3 | 0.3 | 0.3 | 0.3 | 0.3 |
| Monoethanol thio-glycolate | 0.05 | 0.05 | 0.05 | 0.05 | 0.05 | 0.05 | 0.05 |
| Water | ad 100 | ad 100 | ad 100 | ad 100 | ad 100 | ad 100 | ad 100 |
| Results |  |  |  |  |  |  |  |
| Consistency | liquid | liquid | liquid | liquid | liquid | liquid | liquid |
| Appearance | turbid | turbid | clear | clear | clear | clear | clear |
| Consistency with developer | not thick | some what thicker | some what thin | not thick | Significantly thicker | thicker | Thick OK |
| Coloration |  |  |  |  | intensive color result as comparison cream Tab. 4 | intensive color result as comparison cream Tab. 4 | intensive color result as comparison cream Tab. 4 |

*as contemplated herein

Explanation of ingredients (other and/or INCI designation):

Texapon® K12G (BASF): Sodium Lauryl Sulfate (from about 95 to about 99 wt. % active substance)

Comperlan® 100 (BASF): Coconut fatty acid monoethanolamide, Cocarnide MEA (from about 92 to about 99 wt. % active substance)

Dehydol® LS2 Deo N (BASF): Fatty alcohol ($C_{12}$-$C_{14}$)-polyglycolether (2 EO), Laureth-2 (100 wt. % active substance) Eumulgin® 5 (BASF): Oleyl cetyl alcohol ethoxylated (5 EO), Oleth-5Schercemol™ CO Ester (Lubrizol): Hexadecyl 2-Ethylhexanoate, Cetyl Ethylhexanoate Antil® 200 (Evonik): 56 wt. % PEG-200 Hydrogenated Glyceryl palmate, 14 wt. % PEG-7Glyceryl Cocoate, 30 wt. % water Dye precursors, 6.72 wt. % in each case: p-toluylenediamines sulfates 4.4 wt. %, resorcinol 1.56 wt. %, m-aminophenol (155 wt. %, 2-amino-4-hydroxyethylaminoanisole sulfate, 0.21 wt. %, relative to the total weight of the hair dyes in each case.

Furthermore, in Table 1 and 2, the consistency and appearance before mixing with an oxidant preparation determine the consistency immediately after mixing with an oxidant preparation and the coloring performance. The oxidant preparation (developer) which is used is presented in Table 3 below. Compositions 1 to 14 were mixed with the oxidant preparation in a ratio of 1:2 in each case. A clear liquid hair dye which achieved an advantageous consistency for application after mixing with the oxidant preparation was only obtained with the exemplary compositions 12 to 14 (viscosity in the range of 4100 to 6500 mPa s (20° C., measured with the Haake rotation viscosimeter VT550, 20° C., rotation frequency: 8 rpm, rotary measuring system MVII).

Developer and/or oxidant composition:

TABLE 3

| Component | INCI and/or other designation | Developer, 6 wt. % $H_2O_2$ |
|---|---|---|
| Water |  | 81.03 |
| Sodium benzoate |  | 0.04 |
| Dipicolinic acid |  | 0.10 |
| Di-sodium pyrophosphate |  | 0.10 |
| Potassium hydroxide 50% |  | 0.19 |
| Propylene glycol |  | 1.00 |
| HEDP 60% | Etidronic Acid, 1-Hydroxyethylidene-1,1-Diphosphonic Acid | 0.25 |
| Paraffin oil | Paraffinum liquidum | 0.30 |
| Stearyl trimethyl ammonium chloride | Steartrimonium Chloride | 0.39 |
| Cetyl Alcohol/Stearyl Alcohol | Ceteary1 Alcohol | 3.40 |
| Polyoxyethylene (20) Cetylstearyl-ether | Ceteareth-20 | 1.00 |
| Hydrogen peroxide 50% | Hydrogen peroxide 50% | 12.20 |
| Total |  | 100.00 |

In Tables 1 and 2, the coloring results are also presented in comparison with a known, non-liquid dye. The composition of this known cream-like coloring agent is specified in Table 4 below.

TABLE 4

| INCI and/or other designation | Comparison cream |
|---|---|
| Propanediol-1,2 | 9.00 |
| Dehydol ® LS 2 Deo N | 12.00 |
| Disodium Cocoamphodiacetate | 1.25 |
| PEG 40 Castor Oil | 5.00 |
| Dye precursors (like in Tab. 1 and 2) | 6.72 |
| Oleic acid | 11.50 |
| Schercemol ® CO | 1.00 |

TABLE 4-continued

| INCI and/or other designation | Comparison cream |
|---|---|
| Synative ® Al: Lauryl/Myristyl Alcohol | 8.00 |
| Sunflower Oil | 0.50 |
| Ascorbic acid | 0.30 |
| Monoethanol thioglycolate | 0.05 |
| EDTA | 0.20 |
| Monoethanolamine | 6.50 |
| Water | ad 100 |
| Total | 100.00 |

Compositions 12 to 14 were mixed for comparison with the oxidant preparation shown in Table 4 in a weight ratio of 1:2 and applied to human hair, left in place to take effect for 30 minutes at room temperature and rinsed out with water.

Surprisingly, it was found that a higher color intensity was achieved with exemplary compositions 12 to 14 than with use of the cream-like coloring agent presented in Table 4. The hair strands felt well-cared-for with use of exemplary compositions 12 to 14. With composition 14, which contains no anionic surfactants except for the soap formed from oleic acid, the well-cared-for feel of the hair strands was especially pronounced.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A liquid agent for oxidative coloring of keratinous fibers comprising, in a hydrous cosmetic carrier:
   (a) a fatty acid which is liquid at 20° C. and has from about 16 to about 22 carbon atoms in a total amount of from about 0.1 to about 15 wt. % relative to the total weight of the liquid agent,
   (b) an alkanolamine as an alkalizing agent, selected from monoethanolamine, 2-amino-2-methylpropanol and triethanolamine, in an amount such that at least one part of the fatty acid is present in the form of a soap,
   (c) an oil component different from (a) in a total amount of from about 0.05 to about 5 wt. % relative to the total weight of the liquid agent,
   (d) an alkylamidoamine in a total amount of from about 0.05 to about 6 wt. % relative to the total weight of the liquid agent, and
   (e) an oxidation dye precursor,
   wherein the agent does not contain any branched fatty alcohols having about 7 or more carbon atoms, and does not contain any fatty alcohols having a melting point of about 25° C. or higher.

2. The agent according to claim 1 wherein the agent is not present as an emulsion.

3. The agent according to claim 1 wherein the agent has a pH value of from about 8 to about 11, measured at 20° C.

4. The agent according to claim 1, wherein the alkylamidoamine is selected from stearamidopropyl dimethylamine, cocamidopropyl dimethylamines, ricinoleic amidopropyl dimethylamine, isostearamidopropyl dimethylamine, oleamidopropyl dimethylamine, behamidopropyl dimethylamine, oleamidopropyl dimethylamine quaternium-33, behamidopropyl ethyldimonium ethosulfate and combinations thereof.

5. The agent according to claim 1, wherein the agent does not contain any anionic surfactants except for the fatty acid in the form of a soap.

6. The agent according to claim 1 comprising, as a nonionic surfactant, an aklyl- and/or alkenyl monoethanolamide with from about 8 to about 18 carbon atoms in the alkyl chain.

7. The agent according to claim 1 comprising, as a nonionic surfactant, an adduct of from about 1 to about 5 mol ethylene oxide on a linear fatty alcohol with from about 8 to about 22 carbon atoms, in an amount of from about 5 to about 12 wt. % relative to the total amount of the liquid agent.

8. The agent according to claim 1 comprising about 0.8 wt. % or less ammonia, relative to the percentage by weight relative to the liquid agent.

9. The agent according to claim 1 comprising ethanol and/or isopropanol in a total amount of from about 0.5 to about 30 wt. %.

10. The agent according to claim 1 comprising about 0.3 wt. % or less anionic polyacrylates.

11. A combination preparation (kit-of-parts) comprising the liquid agent according to one of claim 1 as a component and an oxidant preparation as an additional component.

12. The combination preparation according to claim 11, wherein the oxidant composition comprises from about 1 to about 15 wt. % hydrogen peroxide (calculated as 100% $H_2O_2$) relative to the weight of the composition.

13. The combination preparation according to claim 11, wherein the oxidant preparation comprises at least one cationic surfactant selected from alkyltrimethylammonium chlorides, dialkyldimethylammonium chlorides and trialkylmethylammonium chlorides, and imidazolium compounds having the INCI names quaternium-27 and quaternium-83, wherein the at least one cationic surfactant is included in a total amount of from about 0.1 to about 4 wt. % relative to the total weight of oxidant preparation.

14. A combination preparation according to claim 11, wherein the oxidant preparation comprises about 0.3 wt. % or less anionic polyacrylates.

15. A method for changing color of keratinous fibers comprising the following method steps:
   mixing an agent according to claim 1 with an oxidant preparation which, relative to its weight, comprises from about 1 to about 15 wt. % hydrogen peroxide (calculated as 100% $H_2O_2$) and comprises a cationic surfactant which is selected from alkyltrimethylammonium chlorides, dialkyldimethylammonium chlorides and trialkylmethylammonium chlorides, and imidazolium compounds having the INCI names quaternium-27 and quaternium-83 to form a mixture,
   followed by immediately applying the mixture on the keratinous fibers,
   allowing the mixture to take effect for from about 5 to about 60 minutes, and
   rinsing out the mixture and drying the keratinous fibers.

16. The agent according to claim 1, wherein the alkylamidoamine is stearamidopropyl dimethylamine.

17. The agent according to claim 1, comprising, as a nonionic surfactant, an aklyl- and/or alkenyl monoethanolamide with from about 8 to about 18 carbon atoms in the alkyl chain.

18. The agent according to claim 1, comprising, as a nonionic surfactant, an aklyl- and/or alkenyl monoethanolamide with from about 8 to about 18 carbon atoms in the alkyl chain in a total amount of from about 1 to about 3 wt. % relative to the total amount of the liquid agent.

19. The agent according to claim 1 comprising, as a nonionic surfactant, an adduct of from about 1 to about 5 mol ethylene oxide on a linear fatty alcohol with from about 12 to about 14 carbon atoms, in an amount of from about 7 to about 10 wt. % relative to the total amount of the liquid agent.

20. The agent according to claim 1 comprising no ammonia.

* * * * *